US00PP19389P2

(12) United States Plant Patent
Trees

(10) Patent No.: US PP19,389 P2
(45) Date of Patent: Oct. 28, 2008

(54) ***GERANIUM* PLANT NAMED 'BALLURSAL'**

(50) Latin Name: *Pelargonium×hortorum*
Varietal Denomination: Ballursal

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/895,120

(22) Filed: Aug. 23, 2007

(51) Int. Cl.
*A01H 5/00* (2006.01)

(52) U.S. Cl. ..... Plt./327

(58) Field of Classification Search ..... Plt./327
See application file for complete search history.

(56) References Cited

U.S. PATENT DOCUMENTS

| | | | | | |
|---|---|---|---|---|---|
| PP10,561 | P | * | 8/1998 | Elsner | Plt./327 |
| PP13,913 | P3 | * | 6/2003 | Fleming et al. | Plt./257 |
| PP14,024 | P2 | * | 7/2003 | Dümmen | Plt./327 |
| PP15,008 | P2 | * | 7/2004 | Utecht | Plt./327 |

OTHER PUBLICATIONS

UPOV ROM GTITM Computer Database, GTI Jouve Retrieval Software 2007/05 Citations for 'Ballursal'.*
Canada Plant Breeders' Rights application No. 07–5864 filed Apr. 12, 2007. Published information from Canada Plant Breeders' Rights Office web site attached.

* cited by examiner

*Primary Examiner*—Wendy C. Haas
(74) *Attorney, Agent, or Firm*—Audrey Charles

(57) ABSTRACT

A new and distinct cultivar of *Geranium* plant named 'Ballursal', characterized by its semi-double type, medium salmon pink-colored flowers, medium green-colored foliage with medium zone, and vigorous, upright growth habit.

1 Drawing Sheet

Latin name of genus and species of plant claimed: *Pelargonium×hortorum.*
Variety denomination: 'Ballursal'.

BACKGROUND OF THE INVENTION

The present invention relates to a new and distinct cultivar of *geranium* plant botanically known as *Pelargonium× hortorum* and hereinafter referred to by the cultivar name 'Ballursal'.

The new cultivar originated in a controlled breeding program in Arroyo Grande, Calif. during June 2003. The objective of the breeding program was the development of *Geranium* cultivars with unique flower coloration, medium green-colored foliage, and a vigorous, upright growth habit.

The new *Geranium cultivar is the result of cross-pollination. The female (seed) parent of the new cultivar is Rocky Mountain™ Light Salmon 'Fisrolisa', U.S. Plant Pat. No.* 13,193, characterized by its semi-double type, medium salmon pink-colored flowers with white-colored margins, medium green-colored foliage with distinct zone, and low-mounded growth habit. The male (pollen) parent of the new cultivar is Survivor® Salmon 'Duevisal', U.S. Plant Pat. No. 14,024, characterized by its semi-double type, light orange red-colored flowers, medium-dark green-colored foliage with faint zone, and upright-rounded growth habit. The new cultivar was discovered and selected as a single flowering plant within the progeny of the above stated cross-pollination during May 2005 in a controlled environment at Arroyo Grande, Calif.

Asexual reproduction of the new cultivar by terminal stem cuttings since May 2005 at Arroyo Grande, Calif. and West Chicago, Ill. has demonstrated that the new cultivar produces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Ballursal' as a new and distinct cultivar of *Geranium* plant:

1. Semi-double type, medium salmon pink-colored flowers;
2. Medium green-colored foliage with medium zone; and
3. Vigorous, upright growth habit.

Plants of the new cultivar differ from plants of the female parent primarily in flower color and growth habit. Plants of the new cultivar have darker salmon pink-colored flowers than plants of the female parent. Plants of the new cultivar differ from plants of the male parent primarily in flower color and intensity of leaf zonation.

Of the many commercially available *Geranium* cultivars known to the inventor, the most similar in comparison to the new cultivar is Rocky Mountain™ Salmon 'Fisromon', U.S. Plant Pat. No. 15,008. However, in side by side comparisons, plants of the new cultivar differ from plants of 'Fisromon' in the following characteristics:

1. Plants of the new cultivar have a flower color different from plants of 'Fisromon'; and
2. Plants of the new cultivar are taller, as measured by height from soil level to top of foliage, than plants of 'Fisromon'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ballursal'. The plants were grown in 4.5 inch pots for 8 weeks in a greenhouse at West Chicago, Ill. Plants were given one pinch at transplant.

DETAILED BOTANICAL DESCRIPTION

Figure 1:
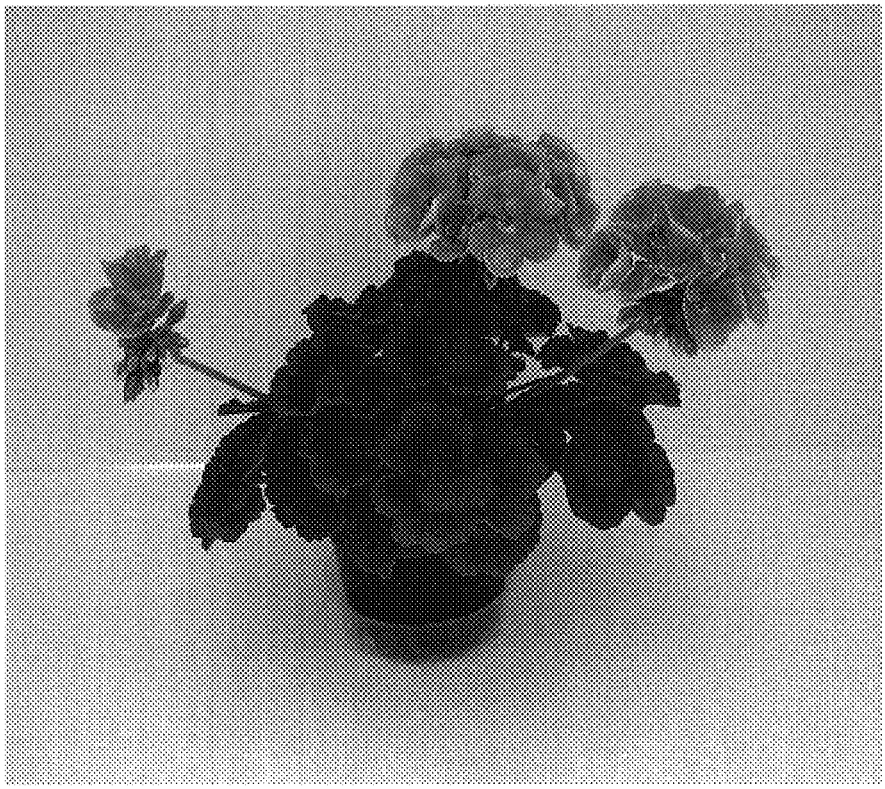
FIG. 1 illustrates a side view of the overall growth and flowering habit of 'Ballursal'.
Figure 2:
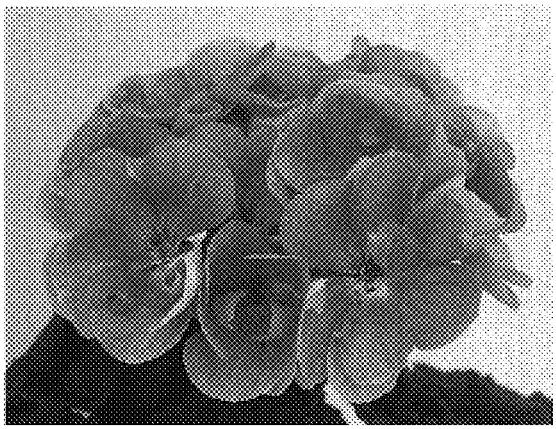
FIG. 2 illustrates a close-up view of an individual umbel of 'Ballursal'.
Figure 3:
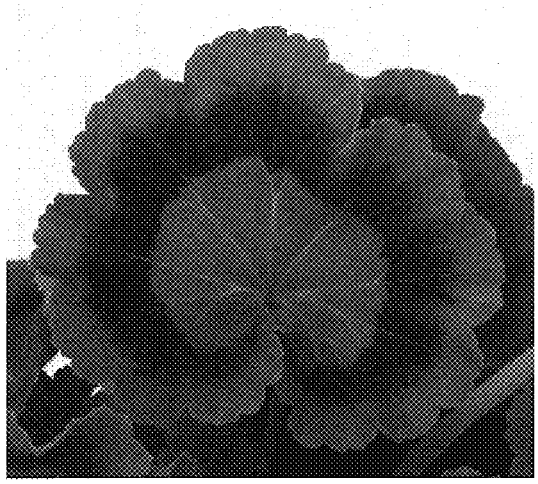
FIG. 3 illustrates a close-up view of an individual leaf of 'Ballursal'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 14, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium×hortorum* cultivar Ballursal.

Parentage:

*Female parent.*—Rocky Mountain™ Light Salmon 'Fisrolisa', U.S. Plant Pat. No. 13,193.

*Male parent.*—Survivor® Salmon 'Duevisal', U.S. Plant Pat. No. 14,024.

Propagation:

*Type cutting.*—Terminal stem.

*Time to initiate roots.*—Approximately 8 to 10 days.

*Time to produce a rooted cutting.*—Approximately 24 to 28 days.

*Root description.*—Fibrous.

*Rooting habit.*—Freely branching.

Plant description:

*Commercial crop time.*—Approximately 8 to 9 weeks from a rooted cutting to finish in a 10 cm pot.

*Growth habit and general appearance.*—Vigorous, upright.

*Size.*—Height from soil level to top of plant plane: Approximately 20.4 cm. Height from soil level to top of foliage: Approximately 13.4 cm. Width: Approximately 26.4 cm.

*Branching habit.*—Freely branching, pinching enhances basal branching. Quantity of main branches per plant: Approximately 3.

*Branch.*—Strength: Strong. Length: Approximately 5.1 cm. Diameter: Approximately 7.0 mm. Length of central internode: Approximately 9.3 mm. Texture: Densely pubescent with a mixture of glandular and nonglandular hairs. Gland color: 27D. Color of young stem: 144C. Color of mature stem: 144A.

Foliage description:

*General description.*—Quantity of leaves per lateral branch: Approximately 6. Fragrance: Slight. Form: Simple. Arrangement: Opposite.

*Leaves.*—Aspect: Petiole is at an acute angle to stem; blade is perpendicular to stem. Shape: Reniform. Margin: Bicrenate, palmately lobed, somewhat wavy. Apex: Obtuse. Base: Cordate. Venation pattern: Palamate. Length of mature leaf: Approximately 7.9 cm. Width of mature leaf: Approximately 8.6 cm. Texture of upper surface: Densely pubescent with a mixture of glandular and nonglandular hairs. Texture of lower surface: Pubescent with a mixture of glandular and nonglandular hairs, dense on venation. Gland color: Colorless, transparent. Color of upper surface of young foliage: 137A with strong zonation of N187A and venation of 144A. Color of lower surface of young foliage: 138A with venation of 138C. Color of upper surface of mature foliage: 137B with strong zonation of N187A and venation of 144A. Color of lower surface of mature foliage: 138B with venation of 138C.

*Petiole.*—Length: Approximately 6.7 cm. Diameter: Approximately 3.0 mm. Texture: Densely pubescent with a mixture of glandular and nonglandular hairs. Gland color: 27D. Color: 144A.

Flowering description:

*Flowering habit.*—'Ballursal' is freely flowering under outdoor growing conditions with substantially continuous blooming from spring through autumn and year-round in greenhouse environment.

*Lastingness of individual flower on the plant.*—Approximately 12 to 14 days.

Inflorescence description:

*General description.*—Type: Umbel. Positioned above foliage. Quantity of fully open umbels per plant: Approximately 2. Quantity of developing umbels per plant: Approximately: 2. Fragrance: Slight. Length or height: Approximately 6.7 cm. Width: approximately 9.6 cm. Quantity of fully open flowers per inflorescence: Approximately 28.

*Peduncle.*—Strength: Strong. Aspect: Erect. Length: Approximately 12.7 cm. Diameter: Approximately 4.0 mm. Texture: Densely pubescent with a mixture of glandular and nonglandular hairs. Gland color: 27D. Color: 144A.

Flower description:

*General description.*—Type: Semi-double.

*Bud.*—Rate of opening: Generally takes 3 to 4 days for bud to progress from first color to fully open flower.

*Bud just before opening.*—Shape: Elliptic. Length: Approximately 1.5 cm. Width: Approximately 8.0 mm. Sepal texture: Densely pubescent with a mixture of glandular and nonglandular hairs. Gland color: 27D. Petal texture: Glabrous. Petal color: 27B.

*Corolla.*—Shape: Round. Diameter: Approximately 4.6 cm. Depth: Approximately 7.3 mm.

*Petals.*—Quantity: Approximately 5 to 8 petals and 1 to 3 irregularly-shaped petaloids per flower. Shape: Obovate. Appearance: Dull. Margin: Entire. Apex:

Obtuse. Base: Attenuate. Length of upper petals: Approximately 2.6 cm. Width of upper petals: Approximately 2.3 cm. Length of lower petals: Approximately 2.4 cm. Width of lower petals: Approximately 2.4 cm. Texture of upper and lower surfaces: Glabrous. Color of upper surface of upper petals when fully open: N155D at base transitioning through 41D to 41C at apex with venation of 42B on lower one-third. Color of lower surface of upper and lower petals when fully open: N155D at base transitioning through 39D to 39C at apex. Color of the upper surface of lower petals when fully open: N155D at base transitioning through 41D to 41C at apex.

*Calyx.*—Shape: 5-pointed star. Diameter: Approximately 2.1 cm.

*Sepals.*—Quantity per flower: Approximately 5. Shape: Lanceolate. Margin: Entire. Apex: Acuminate. Base: Fused. Length of upper sepal: Approximately 1.1 cm. Width of upper sepal: Approximately 5.0 mm. Length of lower sepals: Approximately 1.1 cm. Width of lower sepals: Approximately 3.0 mm. Texture of upper surface: Glabrous. Texture of lower surface: Densely pubescent with a mixture of glandular and nonglandular hairs. Gland color: 27D. Color of upper and lower surfaces: 144A.

*Pedicel.*—Strength: Strong. Aspect: Acute angle to peduncle. Length: Approximately 3.0 cm. Diameter: Approximately 2.0 mm. Texture: Densely pubescent with a mixture of glandular and nonglandular hairs. Gland color: 27D. Color: 144B with an overlay of 185A.

*Reproductive organs.*—Androecium: Quantity of mature stamens: Approximately 7 per flower. Anther shape: Oblong. Anther length: Approximately 2.0 mm. Anther color: 61A. Filament length: Approximately 5.0 mm. Filament color: Pure white with 41B at anther junction. Pollen amount: Scarce. Pollen color: 30C. Gynoecium: Pistil quantity: 1 per flower. Pistil length: Approximately 0.9 cm. Stigma shape: 5 branched. Stigma length: Approximately 2.0 mm. Stigma color: 185A. Style length: Approximately 2.0 mm. Style color: 27C. Ovary length: Approximately 5.0 mm. Ovary texture: Densely pubescent. Ovary color: 143C.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Ballursal', substantially as herein shown and described.

* * * * *